United States Patent [19]

Sinnar

[11] Patent Number: 4,808,824

[45] Date of Patent: Feb. 28, 1989

[54] COMPOSITIONAL STATE DETECTION SYSTEM AND METHOD

[76] Inventor: Abbas M. Sinnar, 6111 Triangle Dr., Columbia, Md. 21044

[21] Appl. No.: 97,691

[22] Filed: Sep. 17, 1987

[51] Int. Cl.[4] .............................................. G01J 1/00
[52] U.S. Cl. .................................. 250/339; 244/134 E
[58] Field of Search ............................... 250/339, 340; 244/134 E

[56] References Cited

U.S. PATENT DOCUMENTS

| | | | |
|---|---|---|---|
| 3,641,349 | 2/1972 | Dahlin | 250/339 |
| 3,693,025 | 9/1972 | Brunton | 250/339 |
| 4,274,091 | 6/1981 | Decker | 250/339 |
| 4,535,241 | 8/1985 | Eberhardt | 250/339 |
| 4,593,533 | 6/1986 | Alsenz | 250/340 |

Primary Examiner—Janice A. Howell
Attorney, Agent, or Firm—Morton J. Rosenberg

[57] ABSTRACT

An ice detection and measurement system (100) is provided to detect the formation of ice and/or water (40) on a surface (49) and measure the thickness thereof. The ice detection and measurement system (100) includes a radiation source (10) having a wide band emission (12) whose bandwidth is in the infrared portion of the electromagnetic spectrum. The wide band infrared emission (12) is directed to a wavelength selector (20) for providing a discontinuous transmission alternating between a pair of narrow band infrared signals each centered at a different predetermined discrete wavelength. The discontinuous alternating signal (22) is applied to optical system (30) where it is divided into two beams (32 and 34) for application to respective detectors (50 and 60). Reference detector (60) includes photoconductive cell (65) for conversion of beam (34) to a reference signal for each of the discrete wavelengths transmitted by beam (34). Test detector (50) includes photoconductive cell (55) for receipt of beam (34) after transmission through the ice and/or moisture (40) formed on the surface (49) of infrared transparent cover (51), for establishing a test signal responsive to infrared radiation absorbed at each of the two discrete wavelengths. The test and reference signals at each of the two discrete wavelengths are compared in microcomputer (70) for detecting and measuring ice accumulation, to distinguish icing, frost and water accumulation, and to monitor the progress of the icing/de-icing process.

20 Claims, 7 Drawing Sheets

COMPOSITIONAL STATE DETECTION SYSTEM AND METHOD

BACKGROUND OF THE INVENTION

1. Field of the Invention

This invention pertains to infrared detection systems. In particular, this invention directs itself to the detection and determination of the compositional states of a chemical compound by measuring the absorption of radiation having a bandwidth within the infrared portion of the electromagnetic spectrum. More in particular, this invention relates to the detection of the presence on a surface of differing phases of a compound, and simultaneously measuring the thickness of each of the phases by comparing the energy absorption at two discrete wavelengths within the infrared portion of the electromagnetic energy spectrum.

Additionally, this invention relates to the detection of ice, frost and/or moisture layers formed on a surface, and the measurement of the thickness of those layers, after detection and measurement of the magnitude of radiation absorbed at each of two discrete wavelengths of infrared radiation. Still further, the subject invention relates to the simultaneous application of two discrete wavelengths of infrared radiation to (1) a reference detector, and, (2) a test detector having a surface upon which there is a formation of ice and/or moisture. Still further, this invention relates to the measurement of the thickness of layers of ice, frost and/or moisture formed on a test surface by comparison of the energy absorbed at two discrete wavelengths of infrared radiation with the absorption characteristics of ice and water at those discrete wavelengths of infrared radiation.

2. Prior Art

Infrared detection systems and detection systems for ice in particular are known in the art. Additionally, infrared detection systems capable of differentiation between ice and water are known in the art. However, while prior art detection systems may use two wavelengths of infrared radiation, they apply one wavelength as a reference signal and the other as a test or measurement signal. Generally, such prior art systems select a wavelength of infrared radiation for the test or measurement signal such that absorption by ice is maximized.

Thus, such prior art systems while being capable of differentiating between ice or water formed on a surface, they could only provide a measurement of ice thickness. In opposition, the subject ice detection and measurement system applies two discrete wavelengths of infrared radiation at the same time to both a reference detector and a test detector. Both wavelengths used by the subject system are applied as detection signals and reference signals, such that the differences between the absorption of infrared radiation by any ice and/or water formed on the test surface at each of the two discrete wavelengths is determined. The subject system is therefore not limited to just determining the presence of ice or water, or the measurement of either one, but provides the detection of both ice and water, a measurement of the thickness of accumulations of both the ice and the water, and therefore, monitors the progress of any icing/de-icing process.

The best prior art known to Applicant includes U.S. Pat. Nos. 2,359,787; 4,054,255; 4,274,091; 4,593,533; 4,578,959; 3,471,698; 3,732,016; 3,735,136; 3,540,025; 2,476,217; 2,446,885; 3,188,828; 3,280,577; and, 3,946,286.

SUMMARY OF THE INVENTION

A method of determining the compositional state of a chemical compound includes the steps of simultaneously applying at least two discrete energy wavelengths within the electromagnetic energy spectrum to (1) the chemical compound for providing a test signal, and, (2) at least one energy detector for providing an energy wavelength reference. The application of the discrete energy wavelengths is followed by the step of detecting the two discrete energy wavelengths passing through or reflected from the chemical composition. The amount of energy absorbed by the chemical composition is established at each discrete energy wavelength and from this, the phase changes and the dimensions of the discrete phases of the chemical compound are determined.

DESCRIPTION OF THE PREFERRED EMBODIMENTS

Figure 1:
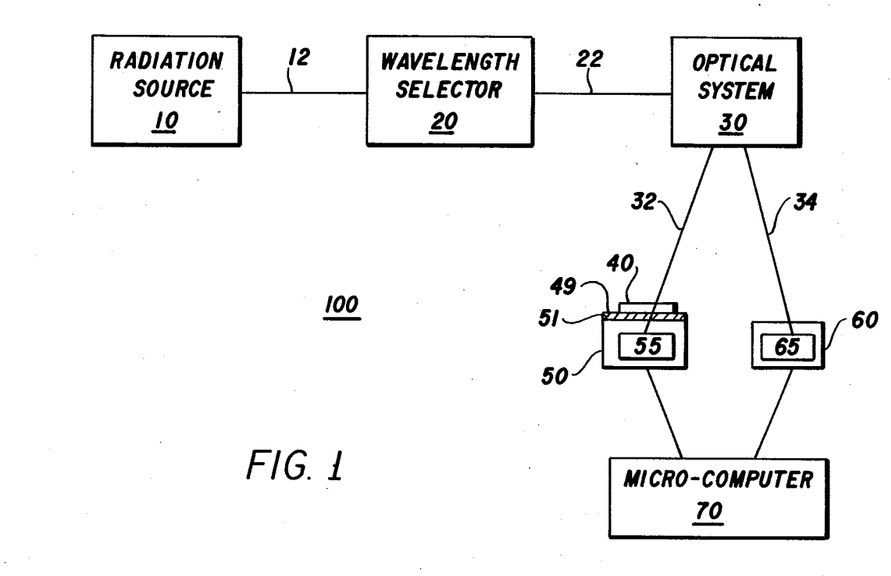
FIG. 1 is an overall block diagram of the compositional state detection system.

Referring now to FIG. 1, there is shown an overall system block diagram of infrared ice detection and measurement system 100 for determining the energy absorption at two discrete wavelengths of infrared radiation for the detection of the presence of moisture and/or ice, and simultaneously measuring the thickness thereof, on a surface such as a highway or airport runway. In overall concept, infrared ice detection and measurement system 100 makes use of infrared radiation absorption by the different phases of a chemical compound at two selected wavelengths within the infrared spectrum, to detect and distinguish between the phases, and measure the accumulation of each respective phase.

Thus, when system 100 is applied to detect the absorption of infrared radiation by a chemical compound such as water at each of two selected wavelengths, it is possible to detect and measure ice accumulation, to distinguish icing and water accumulation, and to monitor the progress of the icing/de-icing process. Infrared icing detection and measurement system 100 provides for an automated method to determine the onset, duration, accumulation, and dissolution of icing on airport runways, aircraft, aircraft navigation structures, and highway surfaces such as bridges and overpasses.

The ability of system 100 to detect the onset of ice formation, as well as monitor the phase change between water and ice, allows for a minimum quantity of de-icing agents to be applied to prevent the formation of any bonding between the ice and the surface being monitored. System 100 has the further ability to monitor the progress of the de-icing process thus, aiding in the assessment of the surface conditions. Thus, infrared ice detection and measurement system 100 can enhance both highway and airport safety while reducing removal equipment requirements, manpower, and chemical costs.

As shown in FIG. 1, system 100 includes radiation source 10 for generating at least two predetermined wavelengths in the infrared region of the electromagnetic energy spectrum. Radiation source 10 is a wide band source of radiation generated from what may be a 100 watt tungsten halogen lamp and infrared glowbar. The infrared emission 12 from radiation source 10 has a bandwidth containing energy whose wavelength covers the range from approximately 1.0 to over 20.0 microns. The wide band infrared emission 12 from radiation source 10 is focused on wavelength selector 20, as is shown in FIG. 1.

Wavelength selector 20 converts the wide band infrared emission 12 to an infrared radiation spectrum having a narrow band signal centered around each of two predetermined wavelengths in an alternate and discontinuous manner. The discrete alternating dual wavelength pulsed output 22 from wavelength selector 20 is focused on optical system 30, which divides the input beam 22 into two output beams 32 and 34.

Optic system 30 may be a prismatic device which divides the alternating dual wavelength input beam 22 into a first alternating dual wavelength output beam 34 directed at reference detector 60, and a second alternating dual wavelength output beam 32 directed at test detector 50. This arrangement provides for two pulsed infrared radiation beams, where both beams 32 and 34 simultaneously alternate between a first predetermined wavelength and a second predetermined wavelength for application to test detector 50 and reference detector 60.

Test detector 50 and reference detector 60 include photoconductor devices 55 and 65, respectively. Photoconductor devices 55 and 65 have a spectral response in the range from approximately 1.0 to over 3.0 microns. It is to be understood that different types of such radiation detectors may be substituted for photoconductor devices 55 and 65 to cover differing or wider ranges of radiation signals. Test detector 50 is designed to be located in close proximity to the surface or equipment whose condition is to be monitored for the onset of ice formation. Thus, test detector 50 is exposed to the same environmental conditions as the surface or equipment being monitored.

Reference detector 60 may be located relatively close to test detector 50, however, it is kept clear of any precipitation or ice formation by heat or other means. Test detector 50 further includes an infrared transparent cover 51 for establishing a surface 49 for the formation of ice and/or moisture through which the second alternating dual wavelength radiation beam 32 will pass. Since the surface 49 of infrared transparent cover 51 is located in the same proximate area as the surface whose condition is being monitored and exposed to the same climatic conditions, the development of ice and/or moisture on surface 49 will be representative of a similar and simultaneous formation on the surface of interest. Thus, second alternating dual wavelength radiation beam 32 being directed to the environmentally exposed surface 49 of infrared transparent cover 51 of test detector 50 will pass through any ice and/or moisture 40 formed thereon.

The transmission of the infrared energy beam 32 through the ice and/or moisture formation 40 is subject to absorption, as is well-known in the art. However, the infrared radiation absorption characteristics for both water and ice change with respect to wavelength, as well as differ from one another throughout most of the spectrum between 1.0 and 2.0 microns. It is the novel approach of infrared ice detection and measurement system 100 to make use of the differing absorption characteristics of both water and ice at two distinct wavelengths within the band of 1.0 to 2.0 microns of the infrared radiation spectrum to substantially enhance simultaneous detection of the presence of both ice and water, if both are present, and calculate the thickness of each.

The output of test detector 50 is therefore responsive to the infrared transmission characteristics of the ice and/or water layer 40, formed on test detector 50, at each of the predetermined wavelengths. First alternating dual wavelength radiation beam 34 is applied to reference detector 60 whose output is responsive to the alternating dual wavelength radiation beam 34 directly, as there is no layer of ice and/or moisture to absorb any of the infrared radiation transmitted.

The outputs of test detector 50 and reference detector 60 are processed in microcomputer 70 to determine the magnitude of energy absorbed at each of the predetermined wavelengths. Detection of a difference between the outputs of test detector 50 and reference detector 60 indicates the presence of moisture and/or ice in the vicinity of the area being monitored. The wavelengths of infrared radiation selected for use by system 100 have been predetermined to maximize the difference in absorption characteristics of ice and water respectively, in order to enhance the accuracy and resolution of the system. As described in following paragraphs, microcomputer can calculate the thickness of the ice and/or water layers when such layers are within the range of microns to several centimeters. Thus, as has been previously stated, system 100 provides a means to detect icing/de-icing onset, monitors its progress, distinguishes between icing and water accumulation, and measures the thickness of both the ice and water layers.

In order to determine the absorption at each of two distinct wavelengths, transmitted in beam 32, they must be processed separately. Thus, the embodiment of system 100 shown in FIG. 1 provides each of the infrared wavelengths to the detectors 50 and 60 in a time multiplex fashion. Wavelength selector 20 in this embodiment alternately provides each infrared wavelength on output beam 22 to optical system 30 for subsequent transmission to both the test detector 50 and reference detector 60. In this manner, the absorption at each of the wavelengths can be measured sequentially and processed in micro-computer 70. Additionally, wavelength selector 20 optically chops the transmission of each wavelength on output beam 22 to provide a pulsed or discontinuous infrared source signal. As is well-known in the art, chopping of an optical signal in this manner provides a means for distinguishing the signal of interest from any background radiation and/or for matching the detector characteristics.

Figure 2:
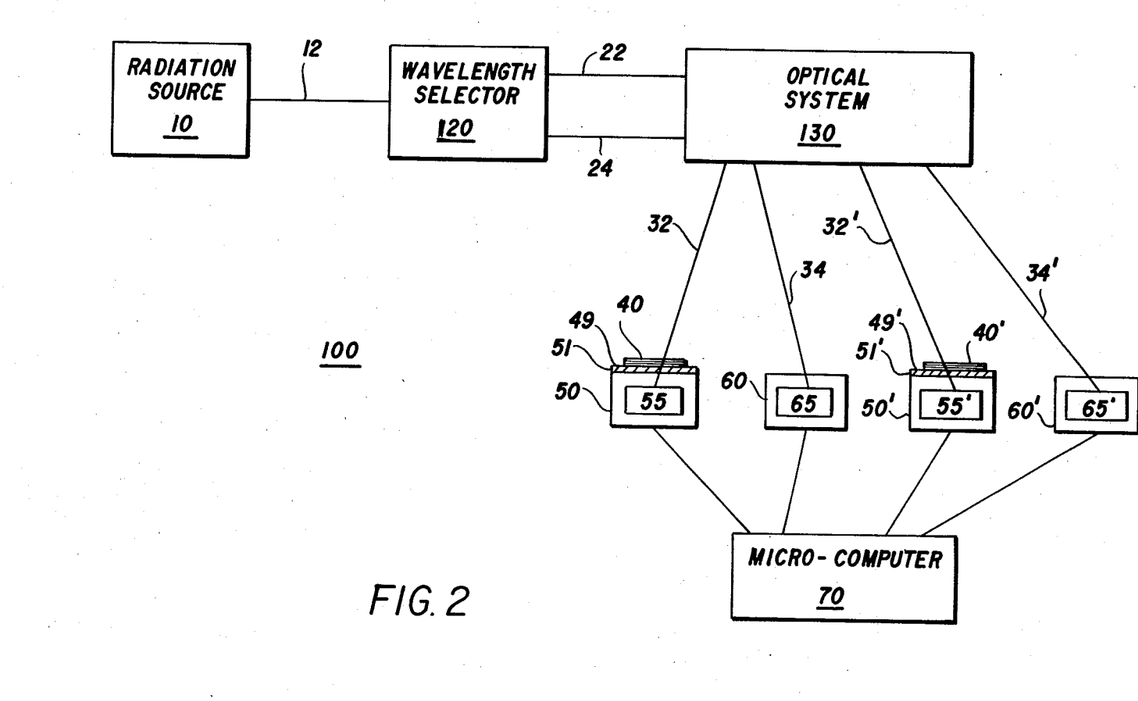
FIG. 2 is an alternate embodiment of the preferred compositional state detection system showing two pairs of test and reference detection mechanisms.

Referring now to FIG. 2, there is shown an alternate embodiment of system 100 where both infrared predetermined wavelengths are transmitted simultaneously through optical system 30 to respective detector elements. The wideband infrared emission 12 from radiation source 10 is focused on wavelength selector 120. Wavelength selector 120 converts the wide band infrared emission 12 to a pair of narrow band signals, each having a wavelength at one of the two predetermined wavelengths within the range of 1 to 2 microns. Each of the two narrow band signals are transmited simultaneously, but separately on output beams 22 and 24 to optical system 130. Both of the narrow band signals transmitted on beams 22 and 24 are optically chopped by wavelength selector 120 to provide a pulsed or discontinuous signal for distinguishing themselves from ambient radiation. Optical system 130 divides each of the narrow band singular wavelength signals separately such that two pairs of narrow band singular wavelength signals result. Each pair of narrow band singular wavelength signals will comprise a first narrow band signal 34 or 34' applied to a reference detector 60 or 60', respectively, and a second narrow band signal 32 or 32' applied to a test detector 50 or 50', respectively.

Thus, both wavelengths of infrared radiation may be transmitted simultaneously from optical system 130, but with each wavelength being directed to separate test detectors 50 and 50' and separate reference detectors 60 and 60'. In this embodiment, both test detectors 50 and 50' are exposed to the climatic environment of the surface or equipment being monitored, while reference detectors 60 and 60' are maintained free of ice and/or moisture to provide a suitable reference signal.

Micro-computer 70 can therefore continuously monitor the outputs of test detector 50 with respect to reference detector 60 and test detector 50' with respect to reference detector 60' and allows microcomputer 70 to determine the absorption of infrared radiation at each of the two predetermined wavelengths by the formation of any ice and/or moisture 40 and 40' formed on respective infrared transparent covers 51 and 51' of test detectors 50 and 50' in a substantially simultaneous time frame.

Figure 3A:
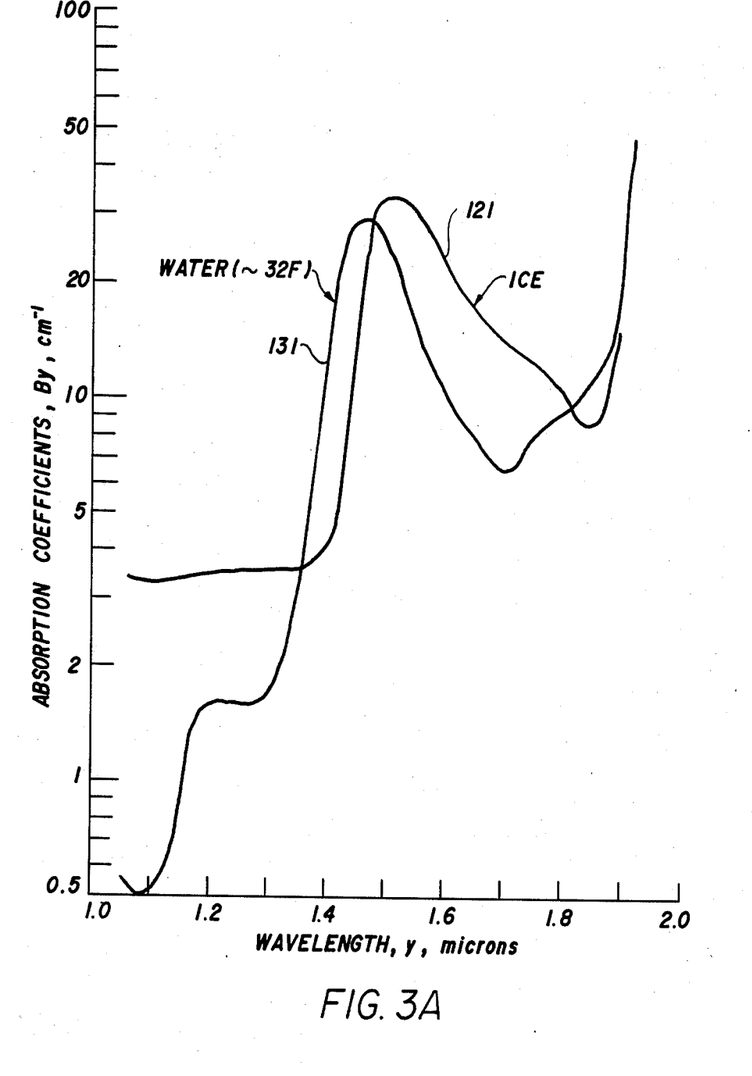
FIG. 3A is a laboratory test graph made by Applicant of absorption coefficients vs. wavelength for both water and ice chemical compounds.
Figure 3B:
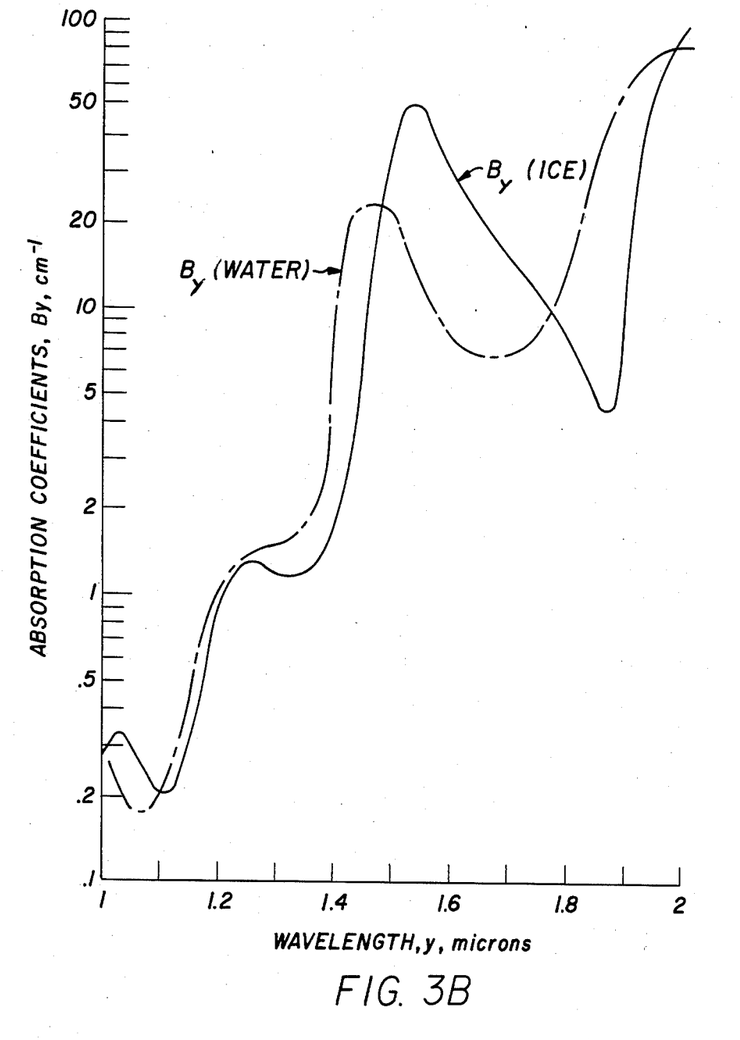
FIG. 3B is a smoothed graph of absorption coefficients vs. wavelength for both water and ice chemical compounds taken from technical literature data.

Selection of the two wavelengths of infrared radiation to be used by system 100 is directly related to the ability of system 100 to differentiate between absorption due to ice vs. that of water. Referring now to FIGS. 3A and 3B, there is shown the absorption coefficients of ice 121 and water 131 with respect to the infrared radiation wavelengths within the range of 1.0 to 2.0 microns. As shown in FIGS. 3A and 3B, the absorption coefficient 121 of ice is two to five times larger than the absorption coefficient 131 of water within the wavelength range of 1.55 to 1.65 microns, whereas around wavelengths of 1.4 and 1.85 microns the absorption coefficient of ice 121 is as much as an order of magnitude smaller than the absorption coefficient of water 131. System 100 provides a device and a method to make use of these crossover absorption characteristics to distinguish icing from water accumulation and in detecting the onset of icing and de-icing processes. In one working embodiment of system 100, the wavelengths selected for the two narrow band infrared radiation beams applied to the test and reference detectors are centered at 1.6 microns and 1.82 microns.

Figure 4:
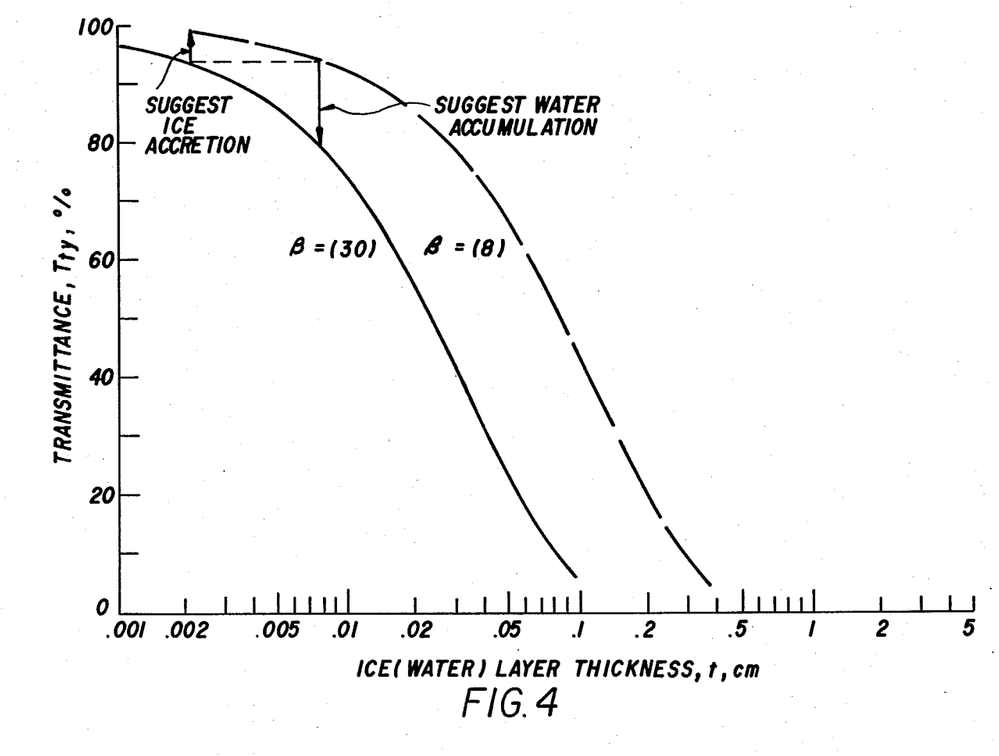
FIG. 4 is a logarithmic graph showing transmittance vs. ice or water layer thicknesses.

The means by which system 100 computes the thickness of any ice and/or water which forms on surface 49 of cover 51 is shown in FIG. 4. FIG. 4 graphically represents the infrared transmittance for ice and water at wavelengths of 1.6 and 1.82 microns, as a function of their layer thicknesses. As shown, the ice thickness from 0.002 cm to 0.1 cm and water thickness from 0.0075 cm to 0.4 cm can be measured as the transmittance decreases from 94 to 5%. As shown, a transmittance of 94% for infrared radiation having a wavelength of 1.6 microns implies both an ice thickness of 0.002 cm and a water thickness of 0.0075 cm.

The transmittance values for ice having a thickness of 0.002 cm and a water layer of 0.0075 cm at a wavelength of 1.82 microns are 98.8% and 79.9%, respectively. Thus, by switching the wavelength from 1.6 microns to 1.82 microns, an increase in transmittance from 94 to 98.8% would indicate that icing is taking place. Conversely, a decrease from 94% to 79.9% on switching wavelengths from 1.6 microns to 1.82 microns would indicate that it is water which is accumulating. Thus, the absorption characteristic differences between ice and water shown in FIGS. 3 and 4 at the selected wavelengths will allow determination of the onset as well as the progress of icing and de-icing processes. For ice layer thicknesses greater than 0.1 cm and water layer thicknesses greater than 0.4 cm, such can be more accurately measured by selecting a different set of wavelength pairs based on their transmittance through thicker layers of ice and water. Using the spectral transmittance equation below, the thickness of ice or water can be computed.

$$T_{ty} = I_{ty}/I_{oy}(1-R) = e^{-B_y t}$$

where:
- $T_{ty}$ = spectral transmittance
- $t$ = thickness of the ice or water layer in cm
- $I_{ty}$ = intensity of radiation beneath the layer of ice or water
- $I_{oy}$ = intensity of radiation incident upon the ice surface (reference level)
- $R$ = fraction of radiation reflected from the surface of the layer which is 2% or less for incident angles between 0° and 60°
- $B_y$ = absorption coefficients Since $B_y$ at any given wavelength y is a constant as given by the curves shown in FIGS. 3A and 3B, the measurement of spectral transmittance can be directly interpreted to represent the icing thickness or water level thickness, depending upon the coefficient used.

The absorption coefficient for frost does not change when wavelengths are switched. Thus, absorption is not a function of wavelength for frost and the thickness of the frost may also be measured from the equation where such exists.

Referring now back to FIG. 1, as previously stated, radiation source 10 is a wideband source of infrared radiation and for one operating embodiment, is a commercially available Oriel Model 7340 Illuminator Housing, switchable 100 watt quartz tungsten-halogen lamp with Oriel Model 6363 infrared glow bar, and a regulated Oriel DC power source model 68735.

Radiation source 10 further includes an optical system for the illuminator which consists of a single concave mirror having a 1.8 magnification which is focused at the monochromator slit of wavelength selector 20.

Figure 5:
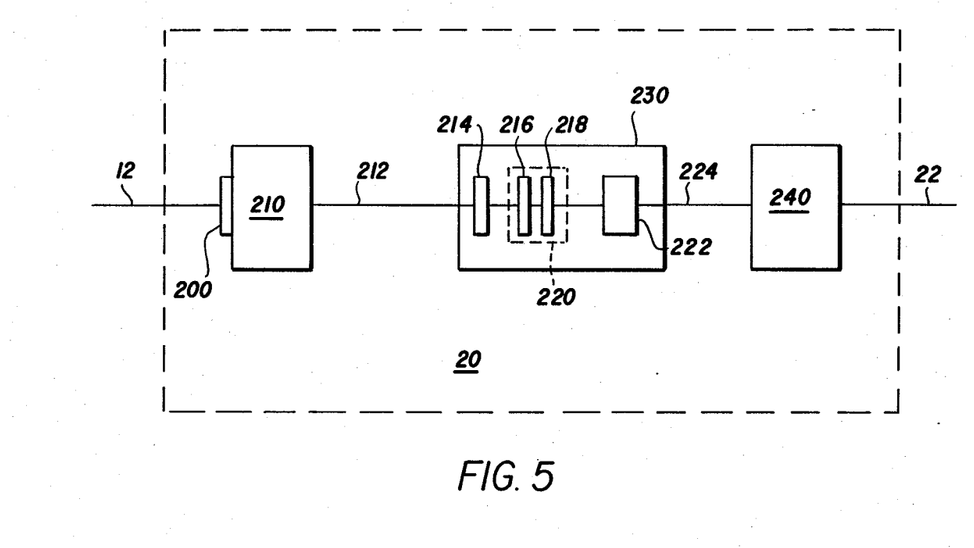
FIG. 5 is a block diagram of the elements provided in the wavelength selector shown in FIG. 1; and, FIG. 6 is a further embodiment of the compositional state detection system showing laser source.

Referring now to FIG. 5, there is shown a block diagram for the wavelength selector 20 used in the embodiment shown in FIG. 1. As shown in FIG. 5, wavelength selector 20 consists of a grating monochromator 210, a filter culminator accessory 230, and an optical chopper 240. The output beam 12 from radiation source 10 is focused on the slit 200 of monochromator 210. The grating monochromator 210 contains gratings and slit widths to provide a radiation spectrum which is less than 0.01 microns in bandwidth, centered around the desired wavelength.

Monochromator 210 is a commercially available Oriel Model 77250 with Oriel grating model 77301, having a usable wavelength region from 0.6 to 2.0 microns. Monochromator 210 provides the desired wavelength outputs by rotation of the grating which is driven precisely to provide a wavelength resolution of 0.2 nanometers. The output of monochromator 210 is passed through filter culminator accessory 230, which is a commercially available Oriel Model 77260 with Iris Diaphragm 214 Oriel Model 2140, to control the beam aperture. The filter portion 220 of filter culminator accessory 230 houses an Oriel Model RG830 long pass filter 216 and an Infrared Industries T-LPG-1 one micron long pass filter 218 to block the undesired second order wavelengths. The filter culminator accessory unit also houses a calcium fluoride culminating lens 222 having a spectral transmission range of 150 nanometers to 9.0 microns.

The output 224 of filter culminator accessory 230 is optically chopped in a digitally controlled chopper 240, which is a commercially available Ithico Model 220 chopper. The optically chopped signal is directed by beam 22 to optical system 30 as shown in FIG. 1. The optically chopped signal 22 is divided into two or more separate beams by optical system 30 shown in FIG. 1. Optically chopped beam 22 is divided into test and reference beams 32 and 34 respectively by a zinc selenide beam splitter. The zinc selenide beam splitter is a commercially available Oriel Model 45363 which is contained in a commercially available Oriel Model 1276 adjustable diameter optic holder.

The inventive concept as herein described discloses a method for determining the compositional state of a chemical compound, used by system 100 to compute the thickness of relatively thin layers of both the solid and liquid phases of water.

A test and reference signal are provided for each of two energy wavelengths within the electromagnetic energy spectrum by applying an optically chopped signal at each of the two discrete energy wavelengths simultaneously to both the chemical compound and a reference detector.

The step of simultaneously applying the two discrete energy wavelengths includes the steps of filtering a wide band source of electromagnetic energy to obtain the two discrete energy wavelengths and establishing at least two distinct optical paths, one for impinging the chemical composition, and the other to provide the energy reference for each of the two chopped discrete energy wavelengths. The method of determining the compositional state of a chemical compound further includes the step of detecting each of the two discrete energy wavelengths after passing through or being reflected from the chemical composition, followed by establishing the amount of energy absorbed by the chemical compound at each of the two discrete energy wavelengths.

The step of establishing the amount of energy absorbed includes the step of comparing the test signal with the energy reference at each of the two discrete energy wavelengths. The final step is to determine the phase changes and dimensions of each of the discrete phases of the chemical compound by comparing the energy absorbed at each of the two discrete energy wavelengths with the absorption characteristics previously established for the chemical compound at each of the two discrete energy wavelengths. Thus illustrates the novel approach for determining the presence of ice and/or moisture on a surface, the accumulated thickness of each, and a direction of the process (icing or de-icing).

The novel approach emphasizes the selection of two signals each at a discrete wavelength where the absorption characteristics of the compositional states to be monitored are significantly different one from the other, and exhibit a cross-over in the absorption characteristics between the two wavelengths selected.

To accomplish this, two narrow band signals each of whose wavelength is centered on one of the selected wavelengths are applied to a test surface, representing the surface being monitored, in an alternating time multiplex manner, as shown in the embodiment of FIG. 1, or simultaneously being applied to two test surfaces as shown in the embodiment of FIG. 2.

Simultaneous to the application of each of the discrete wavelengths being applied to the test surface, a separate discrete wavelength signal is applied to a reference detector to establish a reference level for each wavelength. Discrete wavelength signals applied to both the test surface and reference detector are optically chopped to provide a discontinuous or pulsed signal for differentiation from ambient radiation.

The discrete wavelength signals applied to the test surface, for the embodiments herein described, are transmitted through the test surface to a test detector to establish a signal which is responsive to the absorption of the discrete wavelength signal by the formation of ice and/or moisture on the test surface.

However, it should be noted that the test detector could be located so as to receive a reflection from the test surface to establish a signal responsive to the absorption by any ice and/or moisture formed thereon. The only changes which would be required by this alternate configuration would be in the calculation of the thicknesses of each of the compositional layers, which would have to be reduced by one-half to account for the passage of the discrete wavelength signal passing through those layers twice.

In the embodiments described, detection of the onset of either ice formation or moisture accumulation is easily determined by comparison of outputs from the test detector with that of the reference detector at either of the two wavelengths selected, since any difference would indicate absorption and thus indicate the presence of either the moisture or ice formation. By next comparing the absorption at each of the two wavelengths selected, it can be readily determined whether the absorption is due to ice, moisture, or both, as illustrated in FIGS. 3 and 4. Finally, the thickness of each of the compositional layers can be calculated using the equation for the spectral transmittance and the absorption coefficients for water and ice given in FIGS. 3A and 3B.

Figure 6:
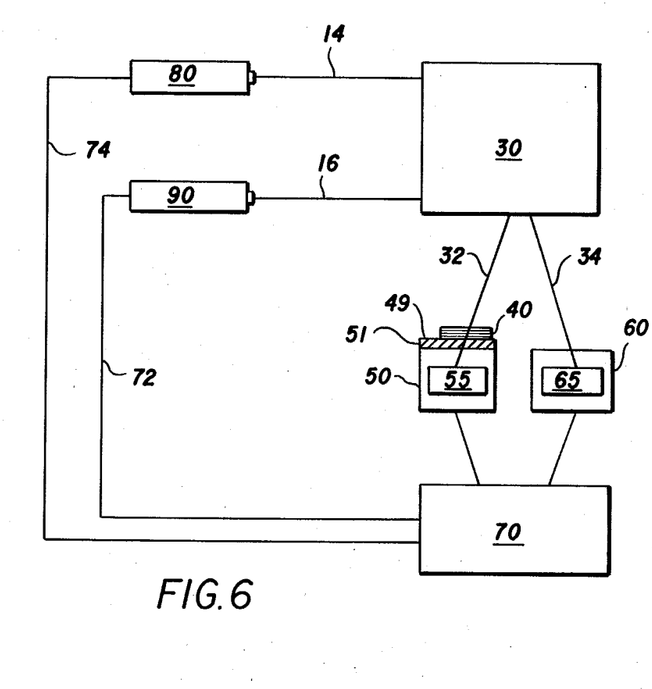

The functions of radiation source 10 and wavelength selector 20, shown in FIG. 1 and radiation source 10 and wavelength selector 120 as shown in FIG. 2, can be replaced by a pair of lasers as shown in FIG. 6.

As shown in FIG. 6, lasers 80 and 90 emit narrow band monochromatic beams 14 and 16 respectively for input to optical system 30. Laser 80 has an infrared emission 14 whose wavelength is centered at 1.6 microns, while laser 90 has an infrared emission 16 whose wavelength is centered at 1.82 microns.

As a replacement for the embodiment shown in FIG. 1, lasers 80 and 90 are operated in an alternating pulsed fashion such that when laser 80 is operating, laser 90 is off and when laser 90 is operating, laser 80 is off. The pulse alternation switching control for lasers 80 and 90 is provided by microcomputer 70 which is coupled to lasers 80 and 90 by respective control links 74 and 72. This permits micro-computer 70 to transmit and synchronously sample the narrow band monochromatic signal at both the test and reference detectors. If the laser arrangement shown in FIG. 6 were applied to the embodiment shown in FIG. 2, then both lasers would be pulsed simultaneously, producing both selected narrow band signals for transmission to the optical system 130 of FIG. 2.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed is:

1. A method of determining the compositional state and any transition between states of a chemical compound comprising the steps of:
    (a) simultaneously applying at least two discrete energy wavelengths within the electromagnetic energy spectrum to (1) said chemical compound for providing a test signal, and, (2) at least one energy detector for providing an energy wavelength reference, each of said discrete energy wavelengths being selected from a wavelength spectrum of absorption for said chemical compound;
    (b) detecting said two discrete energy wavelengths passing through or reflected from said chemical composition;
    (c) establishing the amount of energy absorbed by said chemical compound at each of said discrete energy wavelengths; and,
    (d) determining (1) transitional changes between two states of said chemical compound and (2) a thickness dimension of said chemical compound for each of said two state by (1) comparing said absorbed energy at each of said discrete energy wavelengths with the absorption characteristics of said chemical compound at each of said discrete energy wavelengths for each of said two states and (2) computing said thickness dimensions from a predetermined relationship for said energy absorbed.

2. The method of determining the compositional state of a chemical compound as recited in claim 1 where the step of simultaneously applying said two discrete energy wavelengths includes the step of establishing a discontinuous signal source for each of said energy wavelengths.

3. The method of determining the compositional state of a chemical compound as recited in claim 2 where the step of establishing said discontinuous signal source includes the step of optically chopping said two discrete energy wavelengths.

4. The method of determining the compositional state of a chemical compound as recited in claim 2 where the step of simultaneously applying said two discrete energy wavelengths includes the steps of:
    (a) filtering a wideband source of electromagnetic energy to obtain said two discrete energy wavelengths; and,
    (b) establishing at least two distinct optical paths for (1) impinging said chemical composition, and (2) providing said energy wavelength reference, through division of said discontinuous signal source for each of said wavelengths.

5. The method of determining the compositional state of a chemical compound as recited in claim 2 where one of said discontinuous signal sources has an approximating wavelength at 1.6 microns, and the other of said discontinuous signal sources has an approximating wavelength at 1.82 microns or 1.42 microns.

6. The method of determining the compositional state of a chemical compound as recited in claim 1 where the step of detecting said two discrete energy wavelengths applied to said chemical compound includes the step of applying said two discrete energy wavelengths to an energy detector subsequent to (1) transmission through, or, (2) reflection from said chemical compound.

7. The method of determining the compositional state of a chemical compound as recited in claim 1 where the step of detecting includes the step of applying each of said two discrete energy wavelengths to said reference energy detector in a discrete manner.

8. The method of determining the compositional state of a chemical compound as recited in claim 1 where the step of establishing the amount of energy absorbed by said chemical compound at each of said discrete energy wavelengths includes the step of comparing said test signal with said energy reference at each of said discrete energy wavelengths.

9. The method of determining the compositional state of a chemical compound as recited in claim 1 where the step of simultaneously applying said two discrete energy wavelengths is preceded by the step of selecting said two wavelengths from said wavelength spectrum of absorption for substantially maximizing a difference in absorption between said two states of said chemical compound.

10. The method of determining the compositional state of a chemical compound as recited in claim 1 where said chemical compound is water.

11. A system for comparing the energy absorption at two discrete wavelengths of electromagnetic energy for the detection of the presence of differing phases of a compound, and simultaneously measure the thickness of each of said phases on a surface, comprising:
    (a) energy source means having a signal spectrum in the electromagnetic bandwidth, said signal spectrum having at least two of said discrete energy wavelengths for said comparison of said energy absorptive, said discrete energy wavelengths being selected from a wavelength spectrum of absorption for said differing phases of said compound wherein the difference in absorption between phases is substantially maximized;
    (b) wavelength selection and projection means for establishing a first and second transmission of each of said two discrete energy wavelengths where said first transmission of said two discrete energy wavelengths is a reference signal and said second transmission of said two discrete energy wavelengths is a test signal;

(c) detection means for receiving said reference and test signals, said test signal being received after impingement with said surface; and, (d) processor means for comparing said signals received by said detection means to compute the thickness of each of said phases.

12. The energy absorption comparison system as recited in claim 11 where said energy source is a wide band source of infrared radiation having wavelengths in the approximating range of 1 to 20 microns.

13. The energy absorption comparison system as recited in claim 11 where said energy source comprises a first laser for generating a narrow band emission at one of said two discrete energy wavelengths, and a second laser for generating a narrow band emission at the other of said two discrete energy wavelengths.

14. The energy absorption comparison system as recited in claim 12 where said wavelength selection and projection means comprises:

(a) a monochromator for selecting each of said two discrete energy wavelengths;

(b) a filter assembly for removing undesired second order wavelengths;

(c) a lens assembly for collimating said two discrete energy wavelengths;

(d) an optical chopper for modulating each of said two discrete energy wavelengths to form a pulsed output; and, (e) a beam splitter assembly for dividing each of said two discrete energy wavelengths to form said test signals and said reference signals.

15. The energy absorption comparison system as recited in claim 11 where said detection means includes (1) at least one reference detector for establishing a reference level for each of said two discrete energy wavelengths, and (2) at least one test detector for establishing a detection signal for each of said two discrete energy wavelengths, said detection signal being responsive to absorption of said test signal at each of said two discrete energy wavelengths.

16. The energy absorption comparison system as recited in claim 15 where said processor means includes a microcomputer for comparing said detection signal at each of said two discrete energy wavelengths with the absorption characteristics for each of said phases of said compound to detect said phases and provide said measurement thereof.

17. The energy absorption comparison system as recited in claim 16 where said reference detector includes a lead sulfide photoconductive cell for conversion of said reference signal to said reference level for each of said two discrete energy wavelengths.

18. The energy absorption system as recited in claim 17 where said test detector includes (1) an infrared transparent cover for establishing said surface for the formation of said differing phases of said compound, and (2) a lead sulfide photoconductive cell for conversion of said test signal after impingement with said cover to said detection signal for each of said two discrete energy wavelengths.

19. The energy absorption comparison system as recited in claim 18 where said compound is $H_2O$, and said differing phases comprise a liquid water phase and a solid ice phase.

20. The energy absorption comparison system as recited in claim 19 where said two discrete energy wavelengths comprise a first approximating wavelength at 1.6 microns and a second approximating wavelength at 1.82 microns or 1.42 microns.

* * * * *